United States Patent
Hearn et al.

(10) Patent No.: US 9,918,961 B2
(45) Date of Patent: Mar. 20, 2018

(54) CANNABINOID INHALER AND COMPOSITION THEREFOR

(71) Applicant: Kind Consumer Limited, London (GB)

(72) Inventors: Alex Hearn, London (GB); Ritika Gupta, London (GB); Moira Bowdrey, Cambridge (GB)

(73) Assignee: Kind Consumer Limited, London (GB)

(*) Notice: Subject to any disclaimer, the term of this patent is extended or adjusted under 35 U.S.C. 154(b) by 313 days.

(21) Appl. No.: 14/622,205

(22) Filed: Feb. 13, 2015

(65) Prior Publication Data

US 2015/0231108 A1 Aug. 20, 2015

Related U.S. Application Data

(60) Provisional application No. 61/941,724, filed on Feb. 19, 2014.

(51) Int. Cl.

| | |
|---|---|
| *A61K 31/352* | (2006.01) |
| *A61K 31/05* | (2006.01) |
| *A61K 9/00* | (2006.01) |
| *A61M 15/06* | (2006.01) |
| *A61M 15/00* | (2006.01) |
| *A61K 47/10* | (2017.01) |
| *A61M 11/02* | (2006.01) |

(52) U.S. Cl.
CPC ............ *A61K 31/352* (2013.01); *A61K 9/008* (2013.01); *A61K 31/05* (2013.01); *A61M 15/0093* (2014.02); *A61M 15/06* (2013.01); *A61K 47/10* (2013.01); *A61M 11/02* (2013.01); *A61M 2202/0468* (2013.01)

(58) Field of Classification Search
None
See application file for complete search history.

(56) References Cited

U.S. PATENT DOCUMENTS

2010/0236562 A1* 9/2010 Hearn ................. A61K 9/0043
131/330

FOREIGN PATENT DOCUMENTS

| WO | WO-01/13886 A1 | 3/2001 |
|---|---|---|
| WO | WO-01/66089 A2 | 9/2001 |
| WO | WO-03/055549 A1 | 7/2003 |
| WO | WO-03/055549 A1 | 7/2003 |
| WO | WO-2004/000290 A1 | 12/2003 |
| WO | WO-2004/000290 A8 | 12/2003 |
| WO | WO-2007/002186 A1 | 1/2007 |
| WO | WO-2007/148094 A1 | 12/2007 |
| WO | WO-2011/015826 A1 | 2/2011 |
| WO | WO-2011/107737 A1 | 9/2011 |
| WO | WO-2012/021291 A2 | 2/2012 |
| WO | WO-2012/021291 A3 | 2/2012 |

OTHER PUBLICATIONS

McDerment et al. (GB 2476611 B).*
International Search Report dated Apr. 9, 2015, for PCT Application No. PCT/GB2015/050418, filed Feb. 13, 2015, 5 pages.
Written Opinion dated Apr. 9, 2015, for PCT Application No. PCT/GB2015/050418, filed Feb. 13, 2015, 5 pages.

* cited by examiner

*Primary Examiner* — Robert A Wax
*Assistant Examiner* — Quanglong N Truong
(74) *Attorney, Agent, or Firm* — Mintz Levin Cohn Ferris Glovsky and Popeo, P.C.; Muriel Liberto, Esq.

(57) ABSTRACT

The present invention provides a cannabinoid inhaler, compositions, and methods for delivering a cannabinoid composition to a subject. The cannabinoid composition is delivered in the form of inhaled droplets of respirable size via pulmonary administration. The invention may be used in the treatment of a condition or disorder selected from the group consisting of neuropathic pain, cannabis addiction, nausea, motion sickness, arthritis, and neurodegenerative disease.

13 Claims, 6 Drawing Sheets

CANNABINOID INHALER AND COMPOSITION THEREFOR

CROSS-REFERENCE TO RELATED APPLICATIONS

The present application claims the benefit of priority to U.S. Provisional Patent Application Ser. No. 61/941,724, filed on Feb. 19, 2014. The content of this application is incorporated herein by reference in its entirety.

FIELD OF THE INVENTION

The present invention relates to a cannabinoid inhaler and a composition therefor.

BACKGROUND

Cannabinoids have long been known for their therapeutic potential in pain relief, treatment of seizures, antiemesis et cetera. It is, however, a class of compounds whose usage has been associated with a great deal of debate owing to its psychoactive effects. It was not until the discovery of cannabinoid receptors (CB1 and CB2) and the isolation of individual cannabinoids such as THC (tetrahydrocannabinol), CBD (cannabidiol), CBN (Cannabinol), and THCV (Tetrahydrocannabivarin), that the psychoactive effects could be attributed primarily to compounds (like THC) with high affinities to the receptor CB1. Furthermore, it has been established that individual cannabinoids differ from one another in their affinities to receptors and certain cannabinoids, such as CBD, behave as CB1/CB2 antagonists, thereby blocking some actions of their agonists, such as THC.

With on-going research, therapeutic applications of cannabinoids are becoming increasingly evident, resulting in legalisation of these compounds for medical purposes in a number of countries. The primary targets of research in this field are being associated with safe, rapid and/or effective delivery of cannabinoids.

A number of ways of delivering cannabinoids are known in the art.

For example, US2012/0304990 teaches the use of heating to vaporise a cannabis deposit. One draw back of this system is that there is only a small temperature differential between the temperature at which the cannabis will vaporise (180° C. to 200° C.) and the temperature at which toxins are produced (230° C.).

A number of documents (for example WO03/055549, U.S. Pat. No. 6,509,005 and WO2004/000290) disclose the use of a metered dose inhaler. Such inhalers suffer from a number of drawbacks. Firstly, the metering chamber is relatively small, generally less than 100 µl resulting in delivery of fairly concentrated doses. Also, such devices require users to optimally co-ordinate actuation of the outlet valve and inhalation, failing which, dose delivery could be variable.

A further common mechanism is the simple spray which is disclosed, for example, in WO02/064109 and US2006/135599 which are designed to provide a sublingual or buccal spray. Such a spray is currently being marketed by GW Pharmaceuticals under the Sativex™ brand. These sprays suffer from the possibility of non-uniform drug dose delivery owing to the flushing action of saliva. Further, they have a slower onset of action when compared with pulmonary delivery.

SUMMARY OF THE INVENTION

The present invention provides compositions, devices, and methods for delivering a cannabinoid composition to a subject. Preferably, the cannabinoid composition is delivered in the form of inhaled droplets of respirable size via pulmonary administration. In one embodiment, the subject is a subject in need of prophylaxis or treatment with a cannabinoid. In one embodiment, the subject suffers from a condition or disorder selected from the group consisting of neuropathic pain, cannabis addiction, nausea, motion sickness, arthritis, and neurodegenerative disease. In one embodiment, the neurodegenerative disease is selected from the group consisting of Alzheimer's, Parkinson's and multiple sclerosis. In one embodiment, the invention provides methods of treating a subject suffering from a condition or disorder selected from any of the foregoing. In one embodiment, the invention provides methods of ameliorating one or more symptoms associated with the condition or disorder.

In one embodiment, the cannabinoid composition is delivered to the subject through an inhaler. In one embodiment, the inhaler comprises a housing; a reservoir within the housing, said reservoir containing an inhalable cannabinoid composition; a composition flow path from the reservoir and out of a composition outlet at an inhaling end of the housing; and a non-metered breath operated outlet valve for controlling the flow of the cannabinoid composition through the composition flow path, the inhalable composition comprising a cannabinoid or a pharmaceutically acceptable derivative or salt thereof, and an alcohol. The alcohol can be a monohydric or a polyhydric alcohol. In one embodiment, the alcohol is a monohydric alcohol and the inhalable composition further comprises one or more of a glycol and a glycol ether. In a further embodiment, the ratio of alcohol, which is preferably a monohydric alcohol, to glycol or glycol ether by weight is from 6:1 to 1:1. In one embodiment, the inhalable composition comprises or consists of one or more cannabinoids or pharmaceutically acceptable derivatives or salts thereof; a propellant; a monohydric alcohol; and a glycol and/or glycol ether in a weight ratio of monohydric alcohol to glycol/glycol ether of from 6:1 to 1:1.

In one embodiment, the inhaler further comprises an air flow path from an inlet spaced from the inhaling end of the inhaler to an air outlet at the inhaling end, the air flow path being configured such that suction on the inhaling end causes flow through the air flow path which causes the breath operated valve to open, the air outlet being positioned adjacent to the composition outlet, such that air from the air outlet impinges on the composition leaving the composition outlet. In a further embodiment, there is a respective air flow outlet on either side of the inhalable composition outlet.

In a further embodiment, the outlet valve comprises a flexible diaphragm within the housing positioned so as to be influenced by the air flowing through the air flow path; and a valve element movable with the diaphragm and biased by a biasing force into a position in which it closes the composition flow path, such that suction on the inhaling end causes a flow through the air flow path providing a pressure differential across the diaphragm thereby lifting the valve element against the biasing force to open the composition flow path; and wherein the biasing force is arranged to close the composition flow path once the suction ceases.

In a further embodiment, the inhaler comprises a first air flow path partly defined by one side of the diaphragm, a second air flow path partly defined by the opposite side of the diaphragm, each flow path having an opening at the outlet end, wherein the air flow paths are arranged such that suction at the outlet end results in a pressure differential across the diaphragm that moves the diaphragm and hence moves the valve element against the biasing force to open the composition flow path.

In a further embodiment, at least a portion of the flow path is a deformable tube, and the outlet valve is provided by a clamping member which pinches the deformable tube closed when no suction force is applied to the inhaling end to close the composition flow path and releases the tube to open the composition flow path when suction is applied at the inhaling end.

In a further embodiment, the inhaler further comprises a refill valve in communication with the reservoir via which the reservoir may be refilled. In one embodiment, the reservoir is pressurised. In a further embodiment, the inhalable composition further comprises a propellant. In one embodiment, the propellant is a hydrofluorocarbon. In one embodiment, the propellant is present in an amount from at least 60% w/w, based on the total weight of the composition. In a further embodiment, the size of the reservoir, the pressure within the reservoir, and the size of the composition flow path at its narrowest point are arranged so that, when the outlet valve is fully opened, the reservoir will discharge in less than 30 seconds.

In one embodiment, the inhaler is configured to eject the inhalable composition therefrom in the form of droplets, at least 99% vol of the droplets having a diameter of less than 10 microns.

The invention also provides an inhalable composition comprising one or more cannabinoids or pharmaceutically acceptable derivatives or salts thereof; a propellant; a monohydric or polyhydric alcohol; and a glycol and/or glycol ether, present in a weight ratio of monohydric or polyhydric alcohol to glycol/glycol ether of from 6:1 to 1:1. In a preferred embodiment the alcohol is a monohydric alcohol. In one embodiment, the one or more cannabinoids is selected from tetrahydrocannabinol (THC), cannabidiol (CBD), cannabinol (CBN), tetrahydrocannabivarin (THCV), cannabigerol (CBG), cannabidivarin (CBDV) and cannabichromene (CBC). In one embodiment, the one or more cannabinoids or pharmaceutically acceptable derivatives or salts thereof is present in an amount of from 0.01 to 15 w/w based on the total weight of the composition. In one embodiment, the ratio of monohydric alcohol to glycol or glycol ether by weight is from 5:1 to 1.2:1. In one embodiment, the glycol and/or glycol ether is selected from the group consisting of propylene glycol, polypropylene glycol, polyethylene glycol (PEG), and combinations of two or more thereof. In one embodiment, the glycol and/or glycol ether is propylene glycol and the composition comprises from 0.01 to 5 w/w or from 0.1 to 2% w/w propylene glycol, based on the total weight of the composition. In one embodiment, the monohydric alcohol is ethanol. In one embodiment, the ethanol is present in an amount from 0.5 to 4% w/w, based on the total weight of the composition.

In one embodiment, the composition further comprises a human TAS2R bitter taste receptor agonist, preferably wherein the human TAS2R bitter taste receptor agonist is saccharin. In one embodiment, the composition further comprises saccharin in an amount by weight from 0.001% w/w to 0.1% w/w. In one embodiment, the composition further comprises a flavour component, preferably selected from peppermint oil, aniseed, chocolate, coco, menthol and/or vanillin. In one embodiment, the composition comprises up to 0.1% w/w menthol, based on the total weight of the composition.

The invention also provides a pressurised container containing a cannabinoid composition of the invention. In one embodiment, the container is pressurised to a pressure of from $3 \times 10^5$ Pa to $1.5 \times 10^7$ Pa.

The invention also provides a method of manufacturing a cannabinoid composition of the invention, the method comprising preparing a pre-mixture comprising a monohydric or polyhydric alcohol and a glycol or glycol ether, and optionally a TAS2R taste receptor agonist and/or flavouring component, wherein the ratio of monohydric or polyhydric alcohol to glycol or glycol ether by weight is from 6:1 to 1:1; adding one or more cannabinoids or pharmaceutically acceptable derivatives or salts thereof, to the pre-mixture to obtain a cannabinoid-containing mixture; and adding a propellant to the cannabinoid-containing mixture. In a preferred embodiment the alcohol is a monohydric alcohol. In one embodiment, the composition comprises a TAS2R taste receptor agonist and/or flavouring component, and wherein the monohydric or polyhydric alcohol and glycol or glycol ether are combined before the TAS2R taste receptor agonist and/or flavouring component are added.

The invention also provides an inhaler comprising a cannabinoid composition of the invention.

DETAILED DESCRIPTION

The present invention is particularly concerned with a delivery mechanism and formulation for cannabinoids. The invention provides inhalable cannabinoid compositions, devices for their administration, and methods of use. In accordance with the methods and compositions of the invention, the cannabinoids are delivered directly to the lungs where they are efficiently absorbed into the systemic circulation, resulting in a rapid onset of therapeutic action. The rapid onset of therapeutic action achievable through the compositions and methods of the invention offers an advantage over prior cannabinoid delivery methods such as sublingual or suppository delivery, which generally involve slower systemic absorption. The compositions and methods of the invention also offer the ability to deliver cannabinoids via inhalation at lower temperatures than is possible via the inhalation of cannabinoids vaporised from a cannabis plant surface. In addition, the compositions of the invention administered according to the methods described herein are expected to provide a more uniform and reliable drug absorption profile compared to suppository or sublingual delivery methods. The compositions of the invention may also be administered in a convenient and hygienic manner compared to prior art compositions and delivery methods.

The term "cannabinoid" as used herein may encompass a chemical compound that activates any mammalian cannabinoid receptor, for example human $CB_1$ receptor or human $CB_2$ receptor. As used herein a chemical compound that activates a mammalian cannabinoid receptor includes agonists of said receptor. The skilled person may readily determine whether a compound is a cannabinoid receptor agonist or activator using assays known in the art, for example using a suitable [$^{35}$S]GTPγS binding assay (see, for example Griffin et al, Journal of Pharmacology and Experimental Therapeutics, 285(2), pp. 553-560, 1998. The cannabinoids may be naturally occurring (such as, for example, endocannabinoids or phytocannabinoids) or they may be synthetic. Synthetic cannabinoids may include, for example, the classical cannabinoids structurally related to THC, the non-classical cannabinoids (cannabimimetics) including the aminoalkyindoles, 1,5-diarylpyrazoles, quinolines and aryl-sulphonoamides, and eicosanoids related to the endocannabinoids. When a cannabinoid salt is used, it may be employed in the form of a solution. The one or more cannabinoids is preferably selected from the classical cannabinoids, more preferably selected from tetrahydrocannabinols (THC), preferably delta-9-tetrahydrocannabinol and delta-8-tetrahydrocannabinol, cannabidiol (CBD), cannabinol (CBN), tetrahydrocannabivarin (THCV), cannabigerol (CBG), cannabidivarin (CBDV) and cannabichromene (CBC), cannabicyclol (CBL), cannabichromevarin (CBCV), cannabigerovarin (CBGV and cannabigerol monomethyl ether (CBGM). CBD and THC are particularly preferred cannabinoids in the present invention. In a particularly preferred embodiment, the composition comprises both CBD and THC. CBD typically exhibits only a minimal psychoactive effect. CBD may also act as a potent antagonist to the CB1 receptor, thereby counteracting the psychoactive effect of THC without altering its advantageous clinical effects. The compound "tetrahydrocannabinol" as referred to herein may encompass (−)-(6aR,10aR)-6,6,9-trimethyl-3-pentyl-6a,7,8,10a-tetrahydro-6H-benzo[c]chromen-1-ol.
The compound "cannabidiol" as referred to herein may encompass 2-[(1R,6R)-6-isopropenyl-3-methylcyclohex-2-en-1-yl]-5-pentylbenzene-1,3-diol.

Other cannabinoids suitable for use in the present invention are endocannabinoids, substances that naturally occur in the mammalian body and which activate one or more cannabinoid receptor. Preferably endocannabinoids are selected from arachidonoylethanolamine (AEA), 2-arachidonoylglycerol (2-AG), 2-arachidonyl glyceryl ether (noladin ether), N-arachidonoyl dopamine (NADA), virodhamine (OAE) and lysophosphatidylinositol (LPI).

Synthetic cannabinoids suitable for use in the present invention include nabilone, rimonabant, JWH-073, CP-55940, dimethylheptylpyran, HU-210, HU-331, SR144528, WIN 55,212-2, JWH-133, levonantradol, and AM-2201.

Cannabinoid Inhaler Device

According to the present invention a cannabinoid inhaler comprises a housing; a reservoir within the housing of inhalable composition comprising a cannabinoid or a pharmaceutically acceptable derivative or salt thereof, and an alcohol; a composition flow path from the reservoir and out of a composition outlet at an inhaling end of the housing; and a non-metered breath operated outlet valve for controlling the flow of inhalable composition through the composition flow path.

The use of a non-metered and breath operated valve provides a number of advantages over the prior art dispensers. As the valve is breath operated, it can only be opened when a user is inhaling such that, at the moment the valve opens to release the composition, there is an existing flow of air into the lungs thereby facilitating the entrainment of the composition into the lungs. Further, as the administration of formulation is unmetered, the user can self titrate and can obtain a dose (i.e. one fill of the device) over a number of inhalations (or puffs) at a desired, comfortable pace. This can be done in a few inhalations and potentially in a single inhalation if desired.

Thus, the present invention provides a cannabinoid inhaler which is easy to use and provides a way of obtaining a relatively consistent dose with minimal wastage for deep lung administration and rapid onset of clinical actions as compared to a metered dose inhaler or spray.

The breath-operated valve may have a number of configurations. It may, for example, comprise an electronic flow sensor which detects suction on the inhaling end and activates a solenoid to open the outlet valve. Alternatively, the valve may be a heater which selectively vaporises a proportion of a viscous composition, with the reservoir being configured to replenish the viscous composition in the vicinity of the heater. As a further example, the valve may take the form of a Venturi nozzle which generates a suction force when a user inhales. The suction force may directly remove the composition from the housing, or the valve may further comprise a closure element which is opened by the suction force.

The important consideration for the outlet valve is that it is able to selectively allow the dispensing of composition in response to a user inhaling from the inhaler.

However, preferably, the inhaler further comprises an air flow path from an inlet spaced from the inhaling end to an air outlet at the inhaling end, the air flow path being configured such that suction on the inhaling end causes flow through the air flow path which causes the breath operated valve to open, the air outlet being positioned adjacent to the composition outlet, such that air from the air outlet impinges on the composition leaving the composition outlet.

The provision of an air flow path which both operates the breath operated valve and also impinges on the composition outlet provides a dual benefit in opening the valve and having a beneficial effect on the particle size, as the impinging air breaks up larger droplets of the composition thereby significantly decreasing the mean particle size. If an air flow outlet is provided on either side of the inhalable composition outlet, this effect is enhanced and any deflection of the composition plume caused by a single air outlet is avoided.

The breath-operated valve is preferably provided by a flexible diaphragm within the housing and being positioned so as to be influenced by the air flowing through the air flow path; a valve element movable with the diaphragm and biased by a biasing force into a position in which it closes the composition flow path; wherein suction on the inhaling end causes a flow through the air flow path providing a pressure differential across the diaphragm thereby lifting the valve element against the biasing force to open the composition flow path; and wherein the biasing force is arranged to close the composition flow path once the suction ceases.

The use of a flexible diaphragm is beneficial as it can provide a relatively large surface area so that it is able to open the valve even with a relatively low flow rate. This allows the inhaler to open at a relatively low flow rate as compared to a standard metered dose inhaler which is useful for patients who find it difficult to inhale deeply.

Preferably, the inhaler further comprises a first air flow path partly defined by one side of the diaphragm, a second air flow path partly defined by the opposite side of the diaphragm, each flow path having an opening at the outlet end, wherein the air flow paths are arranged such that suction at the outlet end results in a pressure differential across the diaphragm that moves the diaphragm and hence moves the valve element against the biasing force to open the composition flow path. The presence of the first and second air flow paths minimises further the suction required to open the valve.

Preferably, at least a portion of the flow path is a deformable tube, and the outlet valve is provided by a clamping member which pinches the deformable tube closed when no suction force is applied to the inhaling end to close the composition flow path and releases the tube to open the composition flow path when suction is applied at the inhaling end. The deformable tube provides a simple mechanism for the breath-operated valve which operates particularly well with the flexible diaphragm to provide a simple, reliable and easy to operate breath-operated valve.

The inhaler may be designed for a single use. However, preferably, the inhaler has a refill valve in communication with the reservoir via which the reservoir may be refilled.

The reservoir may be at atmospheric pressure. However, it is preferably pressurised as this pressure can provide the motive force to expel the composition from the reservoir. The reservoir may be pressurised by using a compressed gas. However, preferably, the formulation further comprises a propellant as this allows the pressure in the reservoir to be substantially maintained as the composition is dispensed.

Preferably, the pressure within the reservoir and the size of the composition flow path at its narrowest point are arranged so that, when the outlet valve is fully opened, the reservoir will discharge in less than 30 seconds.

Such a reservoir is an optimal size for cannabinoid delivery as it allows a user to obtain a dose over 8 to 10 puffs, on average. However, the inhaler is not so large that it contains a dose which is likely to be harmful to either the authorised patient or some third party. In view of this, it is not necessary to provide a lock-out mechanism on the inhaler itself.

Preferably, the inhaler is configured to eject inhalable composition therefrom in the form of droplets, at least some of which have a diameter of 10 μm or less, and preferably at least 99% vol of the droplets have a diameter of less than 10 μm.

This relatively small particle size is ideal for pulmonary delivery, and co-operates particularly well with a breath-operated valve to ensure that there is a flow of relatively small particle size delivered into the pre-existing suction air stream ensuring even more reliable and repeatable delivery deep into the lungs.

The inhaler as described herein may comprise the inhalable composition as described herein.

Figure 1:
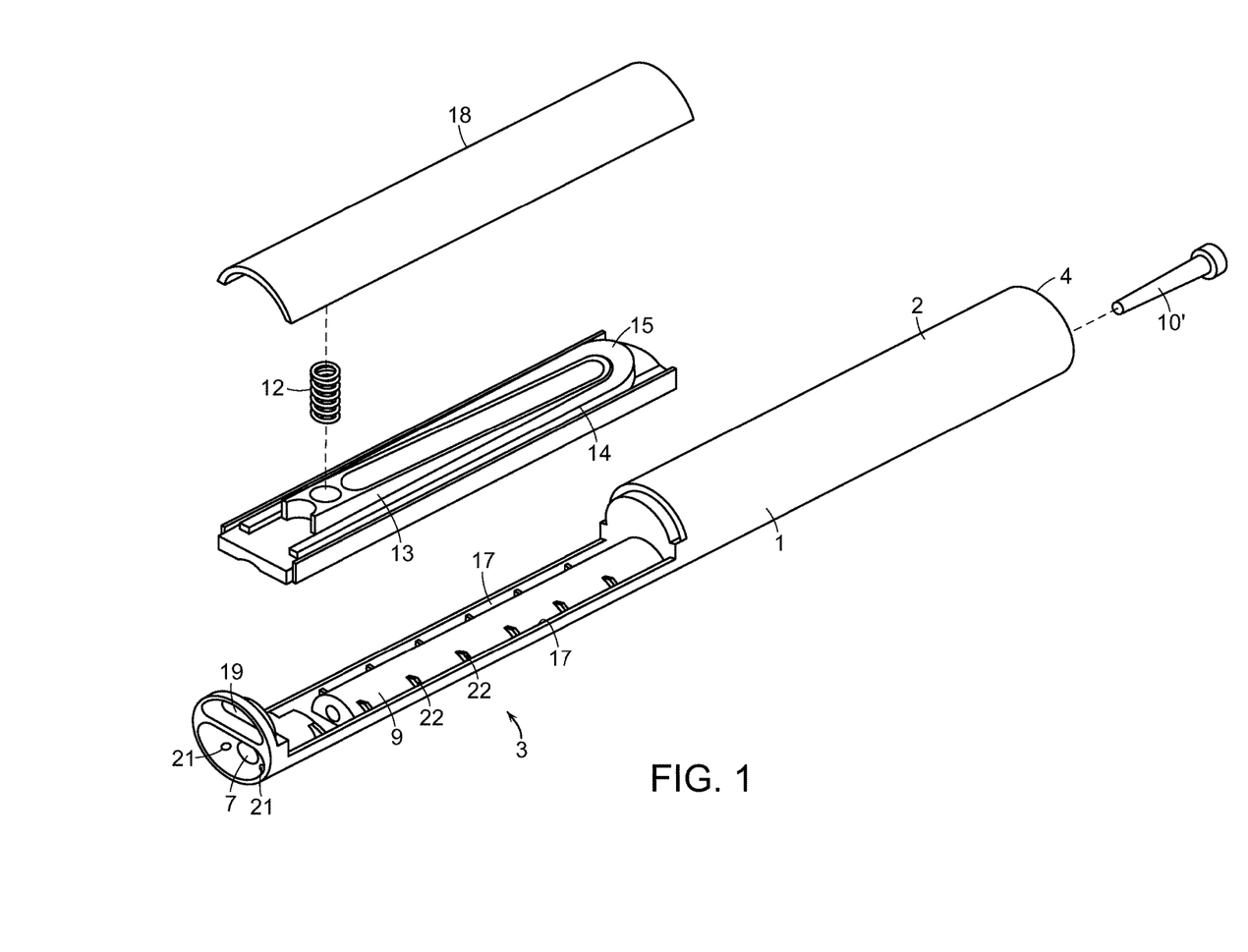
FIG. 1 is an exploded perspective view of an inhaler.
Figure 2:
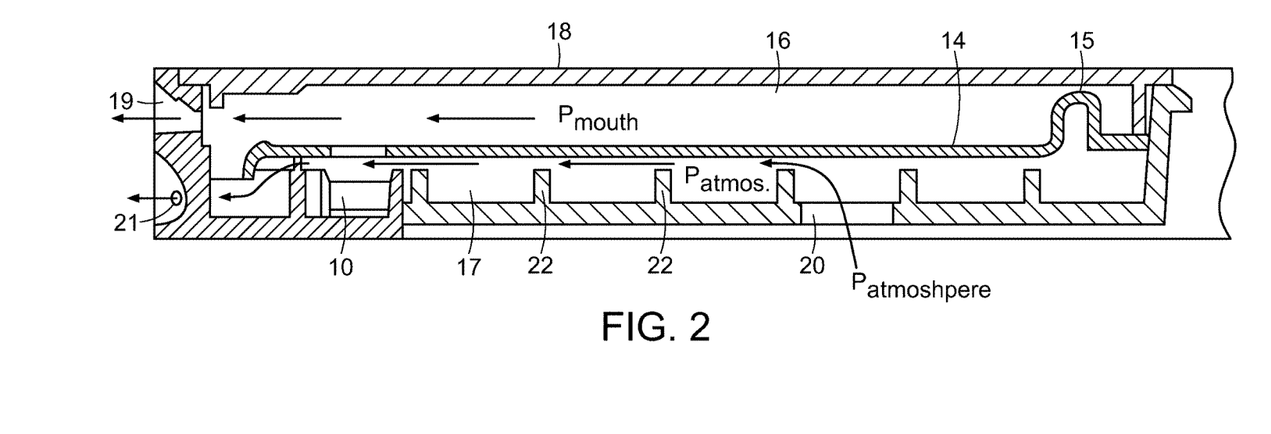
FIG. 2 is a schematic axial cross-section through the outlet end of the inhaler in the plane containing an air flow path and with the vane removed for clarity.
Figure 3:
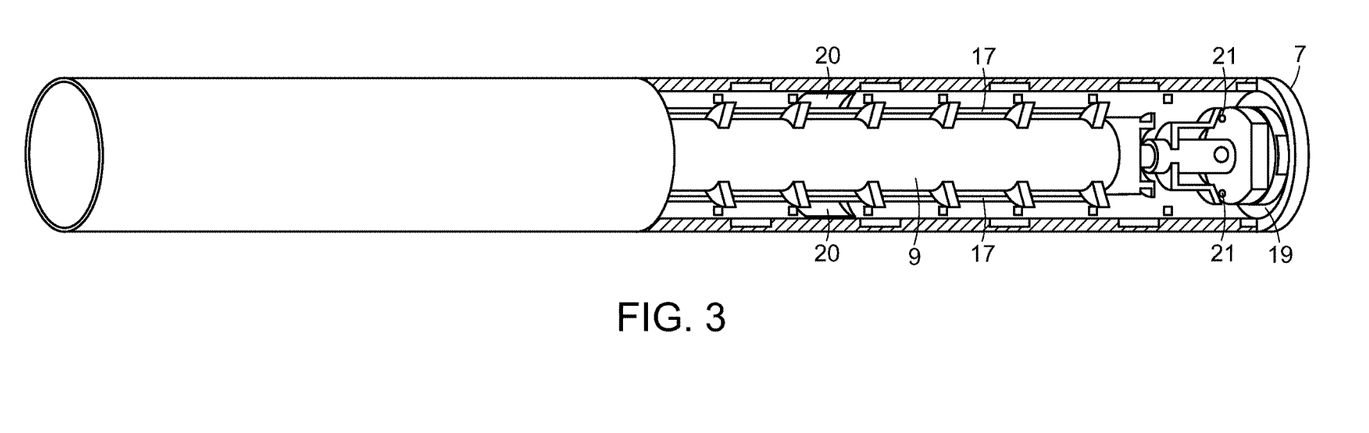
FIG. 3 is a perspective view of the outlet end of the inhaler with the cover, vane and diaphragm removed to show the air flow paths.
Figure 4:
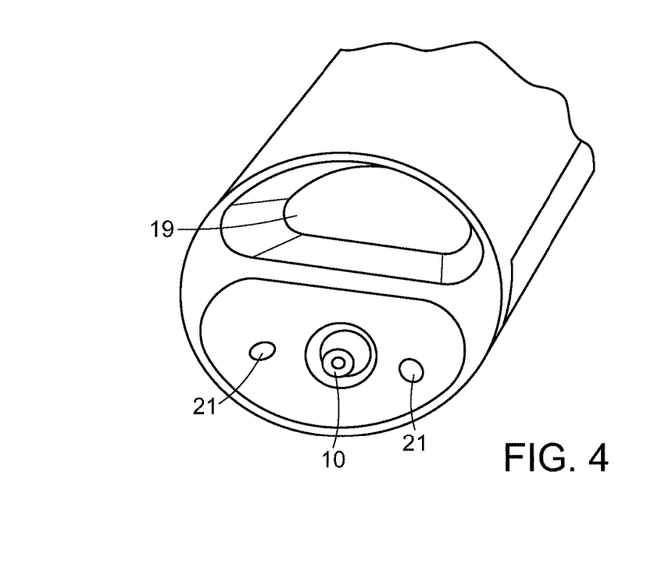
FIG. 4 is a perspective view of the outlet end of the inhaler.
Figure 5:
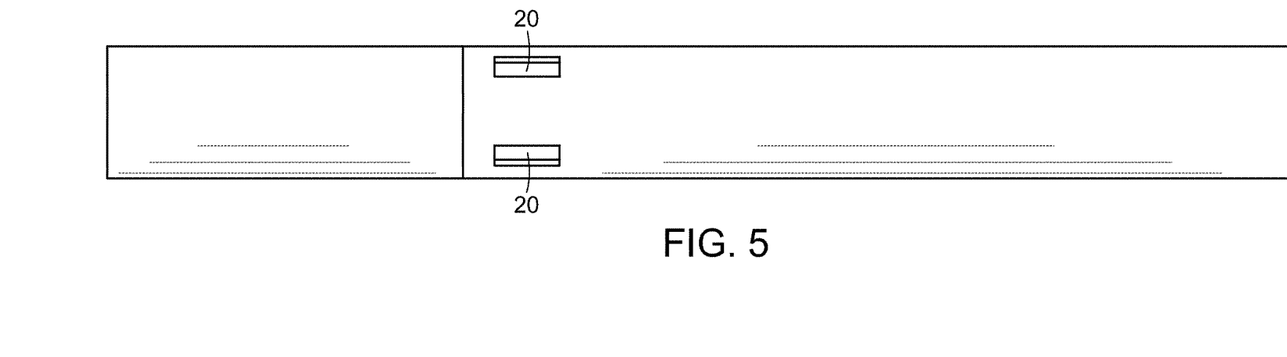
FIG. 5 is a plan view of the inhaler.
Figure 6:
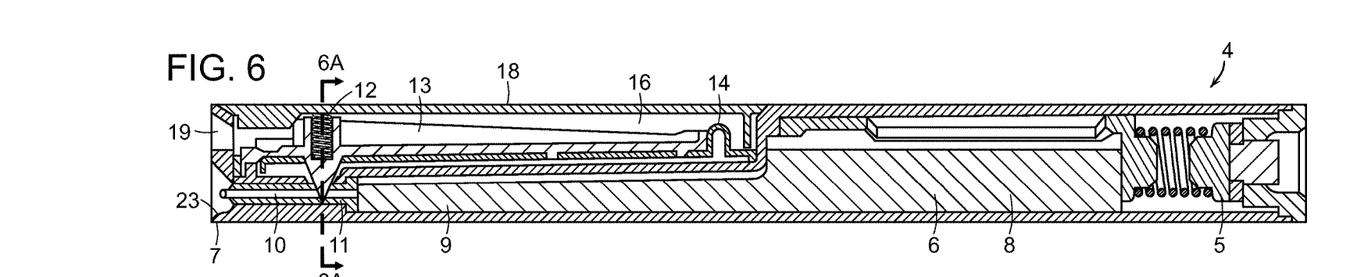
FIG. 6 is a full cross-section of the inhaler.
Figure 6A:
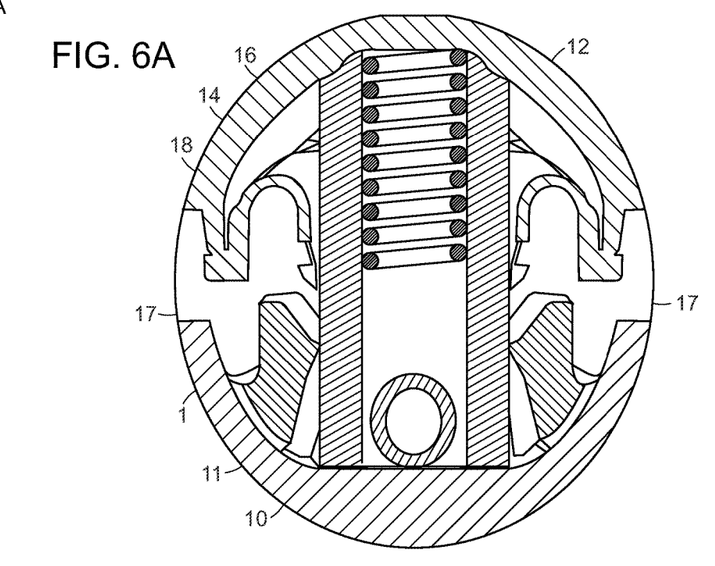
FIG. 6A is a cross-section through line 6A-6A in FIG. 6.

An example of an inhaler in accordance with the present invention will now be described with reference to the accompanying drawings FIG. 1 is an exploded perspective view of an inhaler;

FIG. 2 is a schematic axial cross-section through the outlet end of the inhaler in the plane containing an air flow path and with the vane removed for clarity;

FIG. 3 is a perspective view of the outlet end of the inhaler with the cover, vane and diaphragm removed to show the air flow paths;

FIG. 4 is a perspective view of the outlet end of the inhaler;

FIG. 5 is a plan view of the inhaler;

FIG. 6 is a full cross-section of the inhaler;

FIG. 6A is a cross-section through line 6A-6A in FIG. 6; and

Figure 7:
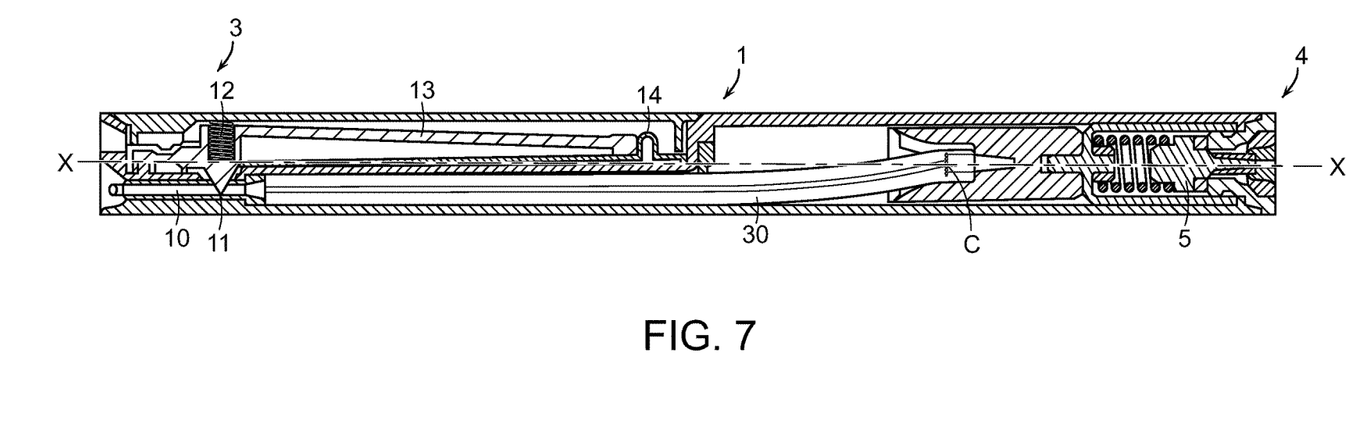
FIGS. 7-9 are cross-sectional views of an inhaler of a second example in various orientations.
Figure 8:
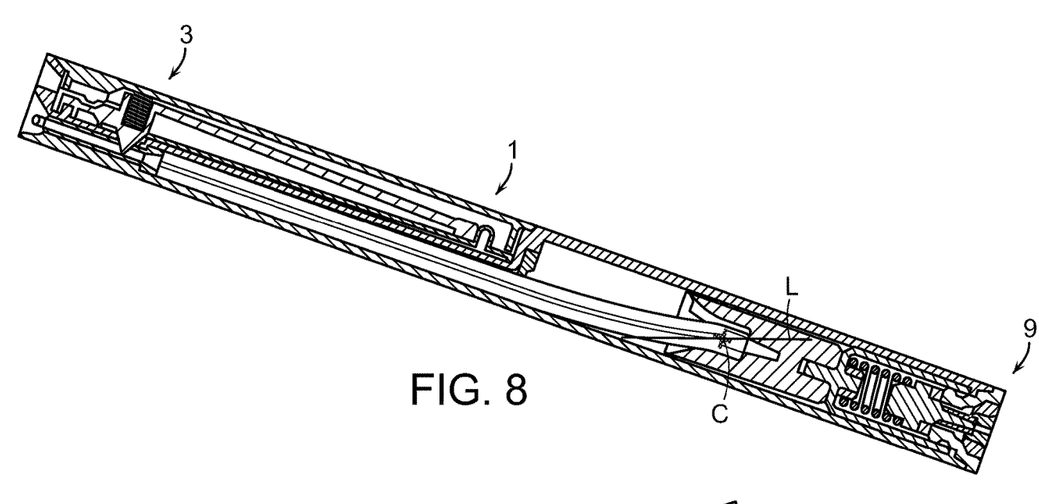
Figure 9:
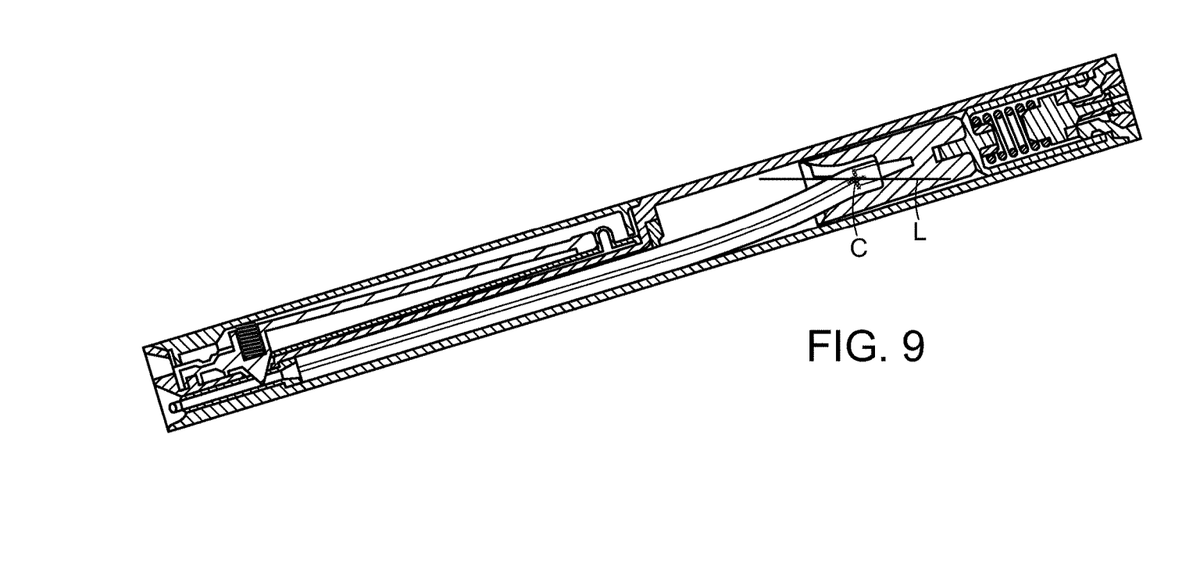

FIGS. 7-9 are cross-sectional views of an inhaler of a second example in various orientations.

The inhaler described below is based on that disclosed in WO 2010/073018. For further details of the device and its refill mechanism, reference is made to WO 2009/001078 and WO 2011/095781.

As shown in FIG. 1, the inhaler comprises a housing 1 which is broadly divided into two parts. The distal part is a reservoir 2 and the proximal part is the breath-activated valve mechanism 3. At the refill end 4 is a refill valve 5 allowing the reservoir to be filled. The reservoir may contain a wick 6 as shown in FIG. 6 and disclosed in WO 2011/107737. At the opposite end is the outlet end 7 which will be described in more detail below.

An elastomeric insert 10 (described in greater detail in GB 1305496.0) in the form of a tube open at both ends is inserted from the distal end. This insert 10 is normally pinched closed by a valve element 11 which is biased downwardly by a spring 12. This pinch closed valve mechanism is described in greater detail in WO 2011/015825.

The valve element 11 is part of a vane 13 which extends along most of the outlet end of the inhaler. The vane 13 is surrounded by a diaphragm 14 which extends across the entire lower face of the vane 13, with the exception of the orifice through which the valve element 11 projects. This valve element is sealed around its periphery to the surrounding housing. At the distal end of the diaphragm 14 is a kink 15 which provides some degree of freedom for the vane 13 to move up and down. The opposite end of the vane 13 is integral with a surrounding frame that is fitted into the housing such that there is a direct connection between the frame and vane to provide a hinge about which the vane pivots.

A mechanism for opening the valve element 11 against the action of the spring 12 will now be described.

This is achieved by first 16 and second 17 air flow paths as best shown in FIG. 2. The first flow path 16 is above the diaphragm 14 with the top of the flow path being formed by housing part 18 which is fixed to the housing 1 once the valve elements are in place. The first air flow path is essentially provided by a first air flow path outlet orifice 19 which leads into the space occupied by the vane 13 above the diaphragm 14. This flow path has no other orifices.

The second air flow path 17 is below the diaphragm 14 and is defined by a pair of second air flow path inlet orifices 20 (only one of which is shown in FIG. 2). In the present example, the second air flow path is actually defined by two separate paths which extend from the inlet orifices 20 along passages 17 which are defined by the housing 1 on the lower surface and the diaphragm 11 at its upper surface and which extends alongside the second portion 9 of the reservoir to the outlet end terminating at a pair of second air flow path outlet orifices 21 which are smaller than the corresponding inlet orifices 20 and are directed towards it to break up the particle size of the composition plume as described in greater detail in GB 1215282.3. The flow through the second air flow path is depicted by arrows in the lower part of FIG. 2 and in FIG. 3. Baffles 22 are provided along the second air flow path 17 to increase the flow resistance in this path.

As a user sucks on the outlet end 7, air is sucked out of the first flow path outlet orifice 19 thereby lowering the pressure in the first air flow path 16. At the same time, air is drawn in through the second flow path air inlet orifices 20. As these are larger than the second flow path outlet orifices 21, a choking effect aided by the baffles 22 effectively causes pressure to increase in the second air flow path. A combination of a reduced pressure above the vane and a raised pressure below the vane 13 causes the vane to be moved upwardly deforming the diaphragm 14 and raising the valve element against the action of the spring 12. When a user stops sucking on the outlet end 7, the pressure above and below the diaphragm 14 equalises and the spring 12 returns the valve element 11 to a position in which it pinches the insert 10 closed.

A second example of an inhaler is shown in FIGS. 7 to 9. This is described in greater detail in GB 1305494.5. In place of the wick 6, this example is provided with a tube 30 having an internal bore 31 leading to the insert 10 at the opposite end of tube 31.

At the inlet end 32 of the tube 30, the bore 31 has an inlet 33 which is supported by a support 34 so that the inlet end 32, and preferably the inlet 33 of the bore 31 is on the main axis X of the housing 1 as shown in FIG. 7.

It will be appreciated from the drawings that the shape of the reservoir is complex. The right hand portion has a generally cylindrical configuration occupying the majority of the diameter of the device while the left hand portion of the reservoir may just be the internal bore 31 of the tube, or there may be a portion of the reservoir on either side of this tube. Further, in the right hand portion, the volume of the reservoir is reduced by the inlet end portion of the tube 30, the support 34, and the refill valve assembly 5. Thus, while the volume of the reservoir 4 can be determined by measuring these components, it may be simpler to determine this experimentally.

The operation of the device will now be described with reference to FIGS. 7 to 9.

When a user sucks on the outlet end 7, the outlet valve 3 opens as previously described. Provided that the inlet 33 of the bore 31 is below the level L of the liquid in the reservoir, the liquid will travel along the bore 31 and will be atomised downstream of the outlet valve element 11 to create a plume for inhalation. FIGS. 7 to 9 show the centroid C of a body of liquid filling the reservoir 4. The inlet 33 of the bore 31 is in the vicinity of the centroid. In this specific example shown in FIG. 1, it is displaced by 1.3 mm from the centroid C towards the refill end 4. In the horizontal orientation shown in FIG. 1, all of the liquid above the level L which represents approximately 50% of the total liquid in the reservoir can be inhaled from the inhaler. When the inhaler is in the tip-down configuration shown in FIG. 2, as the inlet 33 is displaced from the centroid C as described above, slightly more liquid is available than it is in FIG. 1, Conversely, in the tip-up configuration, slightly less liquid is available for inhalation. In a different arrangement, the inlet 33 is at the centroid C, so that there is essentially no variation in dispensing between the three positions. The current preference is for a slight displacement of the inlet 33 towards the refill end from the centroid C as shown as this causes slightly more liquid to be dispensed in the more common tip-down orientation.

Once the cigarette reaches the liquid level position L shown in FIGS. 7 to 9 with the reservoir approximately half full, no further liquid can be inhaled and the inhaler then needs to be refilled via the refill valve 5.

Pressurized Container

In a further aspect, the present invention provides a pressurised container containing the composition as described herein. The pressurised container may be used to release a gaseous flow of the composition to a user. For example, the pressurised container may be provided with means for delivering the contents of the container to the lungs of a user. Such means may take the form of a button, trigger or breath-activated mechanism. The pressurised container may be used to deliver an unmetered dose of cannabinoid to the user. This may be advantageous over prior art methods of cannabis replacement therapy, such as conventional inhalers, nasal sprays, lozenges and patches currently on the market, because it can allow autonomy in cannabinoid replacement regulation, where the user can regulate the amount of compositional cannabinoid he or she wishes to inhale. In addition, the pressurised container can be used as an alternative to recreational smoking of conventional cannabis-containing cigarettes.

The pressurised container of the present invention may be used to release the composition to a user without the need for a separate source of energy. For example, the composition may be released without requiring the heating of substrates, combustion of material or a battery powered electric current. As discussed above, this can result in a reduction in the levels of harmful by-products delivered to a user.

The pressurised container of the present invention may take the form of a pressurised canister, for example, a pressurised aluminium canister. The canister may be fully recyclable and/or reusable. The canister may be refilled as required by a vending machine or a larger container containing the desired composition under a high pressure gradient. In one embodiment, the canister is an AW5052 aluminium canister.

The pressurised container may be capable of dispensing the composition as a mixture of aerosolised droplets. Preferably, the mixture has a particle size distribution that is similar to tobacco smoke. The mixture may have the appearance of a vapour or smoke.

The pressurised container may be pressurised to a pressure of from $3\times10^5$ Pa to $1.5\times10^7$ Pa, preferably from $5\times10^5$ Pa to $2\times10^6$ Pa, more preferably from $5.5\times10^5$ Pa to $1\times10^6$ Pa, even more preferably at about $6\times10^5$ Pa.

Inhalable Cannabinoid Compositions

The compositions of the invention comprise one or more cannabinoids or pharmaceutically acceptable derivatives or salts thereof, a propellant, an alcohol, and a glycol and/or glycol ether. The alcohol may be a monohydric alcohol or a polyhydric alcohol, and is preferably a monohydric alcohol. Monohydric alcohol has a lower viscosity than a glycol or glycol ether. Accordingly, the composition is able to form droplets of a smaller diameter in comparison to compositions in which the monohydric alcohol is not present. The present inventors have surprisingly found that a specific ratio of monohydric alcohol to glycol or glycol ether results in a composition with a desired combination of both long term stability (for example the composition remains as a single phase for at least a week at a temperature of 2-40° C.) and small droplet size. In a preferred embodiment, the ratio of monohydric alcohol:glycol or glycol ether by weight is from 6:1 to 1:1.

The composition preferably comprises from 0.01 to 15% w/w of the one or more cannabinoids or pharmaceutically acceptable derivatives or salts thereof based on the total weight of the composition, more preferably from 0.01 to 10% w/w, even more preferably from 0.1 to 8% w/w, still even more preferably from 1 to 5% w/w.

In one embodiment, the invention provides an inhalable composition comprising:

one or more cannabinoids or pharmaceutically acceptable derivatives or salts thereof;

a propellant;

an alcohol; and a glycol and/or glycol ether, characterised in that the ratio of alcohol:glycol or glycol ether by weight is from 6:1 to 1:1.

In one embodiment, the alcohol is a monohydric alcohol. Preferably the monohydric alcohol is ethanol. Ethanol has a particularly low viscosity in comparison to a glycol or glycol ether, and is therefore particularly effective at enabling the composition to form droplets of small diameter. In addition, ethanol is cheap, relatively non-harmful and readily available. Preferably the composition comprises from 0.5 to 4% w/w ethanol, preferably from 0.75 to 3.5% w/w, more preferably from 1 to 3% w/w based on the total weight of the composition.

In one embodiment, the present invention provides a composition comprising:
 one or more cannabinoids or pharmaceutically acceptable derivatives or salts thereof;
 a monohydric alcohol; and
 a glycol and/or glycol ether, characterised in that the ratio of monohydric alcohol:glycol or glycol ether by weight is from 6:1 to 1:1.

In accordance with the methods and compositions of the invention, the glycol and/or glycol ether may aid the dissolution of the one or more cannabinoids or pharmaceutically acceptable derivatives or salts thereof in the composition. This avoids the presence of precipitates of cannabinoids (or other additives such as saccharin, if present) in the composition, which could cause irritation when delivered to a user. In addition, the presence of glycol or glycol ether reduces the degradation of the cannabinoids that may occur over time, thereby increasing the long-term stability or "shelf life" of the composition.

The glycol and/or glycol ether may be selected from propylene glycol, polypropylene glycol and polyethylene glycol (PEG), or combinations of two or more thereof. Suitably polyethylene glycols may have a molecular mass of less than 20,000 g/mol. An example of a suitable polyethylene glycol is PEG 400. Preferably the glycol or glycol ether is propylene glycol. Propylene glycol provides the composition with a particularly desirable droplet size profile and provides enhanced solvation of excipients and reduces degradation of excipients. Preferably the composition comprises from 0.01 to 5% w/w propylene glycol, more preferably from 0.1 to 3% w/w, even more preferably from 0.3 to 2% w/w.

Preferably the composition further comprises a human TAS2R bitter taste receptor agonist. The use of a human TAS2R bitter taste receptor agonist induces bronchodilation, resulting in a reduction in the levels of delivery-related coughing. Accordingly, a user is more able to tolerate the composition since it causes very little irritation.

The human TAS2R bitter taste receptor agonist may be a naturally occurring compound or a synthetic compound. Examples of suitable naturally-occurring compounds include Absinthin, Aloin, Amarogentin, Andrographolide, Arborescin, Arglabin, Artemorin, Camphor, Cascarillin, Cnicin, Crispolide, Ethylpyrazine, Falcarindiol, Helicin, Humulone isomers, Limonin, Noscapine Papaverine, Parthenolide, Quassin, Sinigrin, and Thiamine. Examples of suitable synthetic compounds include Acesulfame K, Benzoin, Carisoprodol, Chloroquine, Cromolyn, Dapsone, Denatonium benzoate, Dimethyl thioformamide, Diphenhydramine, Divinylsulfoxide, Famotidine, Saccharin, Sodium benzoate, and Sodium cyclamate.

Preferably the human TAS2R bitter taste receptor agonist is saccharin. Saccharin is particularly effective as a human TAS2R bitter taste receptor agonist, may be readily dissolved in the composition, is readily available and provides the composition with a desirable taste profile. Preferably the formulation comprises 0.001% w/w to 0.1% w/w, more preferably 0.003% w/w to 0.01% w/w and even more preferably 0.005% w/w to 0.008% w/w saccharin. Lower levels of saccharin result in a composition with an unacceptable tolerability. Higher levels of saccharin result in an acceptable tolerability but are disfavoured since saccharin they may lead to precipitates of saccharin forming in the composition, which may cause irritation when the composition is administered to a user or blockage when the composition is incorporated into an inhaler. Such weight percentages also provide the composition with an optimised taste profile.

The propellant may be a hydrofluorocarbon, preferably a hydrofluoroalkane, even more preferably 1,1,2,2-tetrafluoroethane (HFA-134a) or 1,1,1,2,3,3-heptafluoropropane (HFC-227). Such compounds are particularly effective as propellants and have no adverse effect on the body.

The composition may comprise at least 60% w/w propellant, more preferably at least 66% w/w, even more preferably from 90 to 99.5% w/w, even more preferably from 92 to 99% w/w, and even more preferably from 96 to 99% w/w, based on the total weight of the composition. The propellant is preferably liquefied. Preferably the composition is a liquid. More preferably the composition is a pressurized liquid.

The composition may further comprise a flavour component. The use of a flavour component may mask the taste of the cannabinoids or derivatives or salts thereof. Suitable flavour components include the flavour components typically added to inhalable products. Examples include carotenoid products, alkenols, aldehydes, esters and delta-lactone flavour constituents. Suitable carotenoid products include beta ionone, alpha ionone, beta-damascone, beta-damascenone, oxo-edulan I, oxo-edulan II, theaspirone, 4-oxo-beta-ionone, 3-oxo-alpha-ionone, dihydroactinodiolide, 4-oxoisophorone, safranal, beta-cyclocitral. Suitable alkenols include $C_4$ to $C_{10}$ alkenols, preferably $C_5$ to $C_8$ alkenols. Specific examples include: cis-2-Penten-1-ol, cis-2-Hexen-1-ol, trans-2-Hexen-1-ol, trans-2-Hexen-1-ol, cis-3-Hexen-1-ol, trans-3-Hexen-1-ol, trans-2-Hepten-1-ol, cis-3-Hepten-1-ol, trans-3-Hepten-1-ol, trans-2-Octen-1-ol, cis-3-Octen-1-ol, cis-5-Octen-1-ol, 1-Octen-3-ol and 3-Octen-2-ol. Suitable aldehydes include benzaldehyde, glucose and cinnamaldehyde. Suitable esters include allyl hexanoate, benzyl acetate, bornyl acetate, butyl butyrate, ethyl butyrate, ethyl hexanoate, ethyl cinnamate, ethyl formate, ethyl heptanoate, ethyl isovalerate, ethyl lactate, ethyl nonanoate, ethyl valerate, geranyl acetate, geranyl butyrate, isobutyl acetate, isobutyl formate, isoamyl acetate, isopropyl acetate, linalyl acetate, linalyl butyrate, linalyl formate, methyl acetate, methyl anthranilate, methyl benzoate, methyl benzyl acetate, methyl butyrate, methyl cinnamate, methyl pentanoate, methyl phenyl acetate, methyl salicylate (oil of wintergreen), nonyl caprylate, octyl acetate, octyl butyrate, amyl acetate (pentyl acetate), pentyl hexanoate, pentyl pentanoate, propyl ethanoate, propyl isobutyrate, terpenyl butyrate, ethyl formate, ethyl acetate, ethyl propionate, ethyl butyrate, ethyl valerate, ethyl hexanoate, ethyl heptanoate, ethyl octanoate, ethyl nonanoate, ethyl decanoate, ethyl dodecanoate, ethyl myristate, ethyl palmitate. Suitable delta-lactone flavour constituents include delta-Hexalactone, delta-Octalactone, delta-Nonalactone, delta-Decalactone, delta-Undecalactone, delta-Dodecalactone, Massoia lactone, Jasmine lactone and 6-Pentyl-alpha-pyrone. Flavour components may serve to mask the taste of cannabinoids.

The flavour component is preferably menthol and/or vanillin. The presence of menthol, together with the saccharin, reduces the irritation experienced by a user. Preferably the composition comprises up to 0.1% w/w menthol, preferably from 0.01% w/w to 0.08% w/w, more preferably from 0.02% w/w to 0.06% w/w, even more preferably from 0.03% w/w to 0.05% w/w, still even more preferably about 0.04% w/w, based on the total weight of the composition.

In a particularly preferred embodiment, the invention provides an inhalable composition comprising;
One or more cannabinoids,
A propellant comprising HF-134a,
Ethanol, and
Propylene glycol, characterized in that the ratio of ethanol to propylene glycol by weight is from 6:1 to 1:1. Even more preferably the one or more cannabinoids are selected from THC and CBD, or a mixture thereof. Preferably each component of the inhalable composition is present in the preferred proportions disclosed herein. Even more preferably the one or more cannabinoids are present from 0.01 to 15% w/w, the propellant is present in at least 66% w/w, ethanol is present from 0.5 to 5% w/w and the propylene glycol is present from 0.01 to 5% w/w. The cumulative proportions of all components present in the composition must add up to 100% w/w.

In a further embodiment of the invention, the inhalable composition consists essentially of the components described herein.

In a further embodiment of the invention, the inhalable composition consists of the components described herein.

Methods of Delivery

The present invention provides methods of delivering a cannabinoid composition to a subject by inhalation with an inhaler device. In contrast to compositions of the prior art, the compositions of the present invention form small diameter droplets without the use of organic acids, resulting in less irritation to the airways. Accordingly, the methods of the invention comprise methods for reducing discomfort and local irritation due to administering a cannabinoid composition by inhalation, the methods comprising administering a cannabinoid composition lacking organic acids.

The composition of the present invention may be delivered to a user via oral inhalation, specifically via pulmonary administration. Accordingly, it is effective for use in cannabis replacement therapy or as an alternative to recreational smoking of cannabis plant material, since it mimics some of the habitual aspects of cannabis smoking.

In accordance with the methods of the invention, the cannabinoid composition comprises a monohydric alcohol and glycol or glycol ether in a ratio of from 6:1 to 1:1. As discussed above, the ratio of monohydric alcohol to glycol ether by weight results in a combination of both stability and a desired droplet size profile. Preferably the ratio of monohydric alcohol:glycol or glycol ether by weight is from 5:1 to 1.2:1.

In one embodiment, the cannabinoid composition is delivered via a conventional pressurised metered-dose inhaler (pMDI), and the composition is delivered in the form of droplets, some of which (such as, for example, at least 10% vol) have a diameter of less than 10 μm, typically less than 5 μm. (The term "diameter" as used herein is taken to mean the largest dimension of a droplet, and is measured using a Malvern Spraytec equipment, if necessary using a flow adaptor to ensure a total flow rate of at least 15 L/min through the equipment) Typically, the majority (such as, for example, at least 50% vol) of the droplets have a diameter of less than 5 μm, typically substantially all (such as, for example, at least 90% vol, or even at least 95% vol) of the droplets have a diameter of less than 5 μm. Advantageously, when administered to a user, droplets with a size of less than 10 μm tend to be deposited in the lungs, rather than, for example, the oropharynx. Accordingly, at least some (such as, for example, at least 10% w/w), typically substantially all (such as, for example, at least 90% w/w), of the cannabinoid enters the bloodstream via the pulmonary route, which results in rapid absorption of the composition.

Typically at least some (such as, for example, at least 10% vol) of the droplets have a diameter of from 0.5 to 3 μm. Such droplets may be deposited in the deep lung, and are therefore particularly able to enter the blood stream via the pulmonary route. Typically at least some (such as, for example, at least 10% vol) of the droplets have a diameter of from 0.4 to 0.5 μm.

In another embodiment, the cannabinoid composition is delivered via an inhaler device described herein. In accordance with this embodiment, the droplets may exhibit the following droplet diameter distribution:

Dv 90 of less than 20 μm, typically less than 10 μm, more typically less than 8, even more typically less than 6 μm, and/or Dv 50 of less than 6 μm, typically less than 4 μm, more typically less than 3 μm, even more typically less than 1 μm, and/or Dv 10 of less than 4 μm, typically less than 2 μm, more typically less than 1 μm, even more typically less than 0.5 μm.

The term "Dv10" as used herein refers to a droplet diameter that 10% vol of the droplets in a composition have a smaller diameter than. The term "Dv50" as used herein refers to a droplet diameter that 50% vol of the droplets in a composition have a smaller diameter than. The term "Dv90" as used herein refers to a droplet diameter that 90% vol of the droplets in a composition have a smaller diameter than. Dv10, Dv50 and Dv90 values may be determined using a Malvern Spraytec device.

Methods of Manufacture

In a further aspect the present invention provides a method of manufacturing the composition described herein, the method comprising:

preparing a pre-mixture comprising a monohydric or polyhydric alcohol and a glycol or glycol ether, and optionally a TAS2R taste receptor agonist and/or flavouring component, wherein the ratio of monohydric or polyhydric alcohol:glycol or glycol ether by weight is from 6:1 to 1:1;

adding one or more cannabinoids or pharmaceutically acceptable derivatives or salts thereof, to the pre-mixture to obtain a cannabinoid-containing mixture; and adding a propellant to the cannabinoid-containing mixture. In a preferred embodiment the alcohol is a monohydric alcohol.

If the cannabinoid is added before the alcohol and glycol or glycol ether are combined, then precipitation of cannabinoid may occur. Likewise, if the composition comprises other components, such as a flavouring component or a TAS2R taste receptor agonist, then these components should be fully mixed into the pre-mixture before the cannabinoids is added in order to avoid precipitation of cannabinoids. In particular, it has been found that when the composition comprises menthol, the menthol should be fully dissolved into the pre-mixture before the cannabinoids is added in order to avoid precipitation of the cannabinoids.

When the composition is to include a TAS2R taste receptor agonist and/or a flavouring component, preferably the monohydric or polyhydric alcohol and glycol or glycol ether are combined before the TAS2R taste receptor agonist and/or a flavouring component are added. This avoids precipitation of the flavouring component or TAS2R taste receptor agonist.

Methods of Treatment

In a further aspect, the present invention provides a method of treating a condition selected from: neuropathic pain, cannabis addiction, nausea, motion sickness, arthritis and neurodegenerative diseases such as Alzheimer's, Parkinson's and multiple sclerosis using the composition as described herein.

The inhalable compositions described herein will now be further described with reference to the following non-limiting examples.

Example 1

0.8 g of the following composition was prepared:
CBD: 9.185 mg
THC: 0.415 mg
Ethanol: 18 mg
Propylene glycol: 15 mg
Menthol: 0.32 mg
Saccharin: 0.05 mg
HFA-134a: 0.77 g THC and CBD were present in a ratio of 23:1 and account for 1.25% w/w of the composition. This composition is considered to be particularly effective for the treatment of neuropathic pain.

Example 2

0.8 g of the following composition was prepared:
THC: 16 mg
CBD: 80 mg
Ethanol: 24 mg
Propylene Glycol: 16 mg
Menthol: 0.4 mg
Saccharin: 0.0504 mg
HFA-134a: 0.664 g The cannabinoids account for 12% of the formulation weight. This composition is considered to be particularly effective for the treatment of nausea, motion sickness or other similar conditions.

Example 3

0.8 g of the following composition was prepared:
THC: 0.25 mg
CBD: 5 mg
Ethanol: 16 mg
Propylene Glycol: 12 mg
Menthol: 0.32 mg
Saccharin: 0.0504 mg
HFA-134a: 0.766 g The cannabinoids are in a ratio of 20:1. This composition is considered to be particularly effective for the relief of the symptoms of arthritis.

Example 4

0.8 g of the following composition was prepared:
CBD: 9 mg
THC: 1 mg
Ethanol: 15 mg
Propylene glycol: 14.6 mg
Menthol: 0.35 mg
Saccharin: 0.05 mg
HFA-134a: 0.76 g The cannabinoids CBD and THC account for 1.25% of the formulation weight. This composition is considered to be particularly effective for reducing the symptoms of Alzheimer's disease.

The invention claimed is:

1. A cannabinoid inhaler comprising:
   a housing;
   a reservoir within the housing containing an inhalable composition comprising a cannabinoid or a pharmaceutically acceptable derivative or salt thereof, and an alcohol;
   a composition flow path from the reservoir and out of a composition outlet at an inhaling end of the housing; and
   a non-metered breath operated outlet valve for controlling the flow of inhalable composition through the composition flow path,
   wherein:
   the breath operated inhaler further comprises an air flow path from an inlet spaced from the inhaling end of the inhaler to an air outlet at the inhaling end, the air flow path being configured such that suction on the inhaling end causes flow through the air flow path which causes the breath operated valve to open, the air outlet being positioned adjacent to the composition outlet, such that air from the air outlet impinges on the composition leaving the composition outlet;
   there is a respective air flow outlet on either side of the inhalable composition outlet; and
   the air flow outlets are directed towards a composition plume emitted, in use, from the inhaler to break up the particle size of the composition plume.

2. An inhaler according to claim 1, wherein the outlet valve comprises
   a flexible diaphragm within the housing and being positioned so as to be influenced by the air flowing through the air flow path;
   a valve element movable with the diaphragm and biased by a biasing force into a position in which it closes the composition flow path;
   wherein suction on the inhaling end causes a flow through the air flow path providing a pressure differential across the diaphragm thereby lifting the valve element against the biasing force to open the composition flow path; and
   wherein the biasing force is arranged to close the composition flow path once the suction ceases.

3. An inhaler according to claim 2, further comprising a first air flow path partly defined by one side of the diaphragm, a second air flow path partly defined by the opposite side of the diaphragm, each flow path having an opening at the outlet end, wherein the air flow paths are arranged such that suction at the outlet end results in a pressure differential across the diaphragm that moves the diaphragm and hence moves the valve element against the biasing force to open the composition flow path.

4. An inhaler according to claim 1 wherein at least a portion of the flow path is a deformable tube, and the outlet valve is provided by a clamping member which pinches the deformable tube closed when no suction force is applied to the inhaling end to close the composition flow path and releases the tube to open the composition flow path when suction is applied at the inhaling end.

5. An inhaler according to claim 1 further comprising a refill valve in communication with the reservoir via which the reservoir may be refilled.

6. An inhaler according to claim 1, wherein the reservoir is pressurised.

7. An inhaler according to claim 6, wherein the inhalable composition further comprises a propellant.

8. An inhaler according to claim 7, wherein the size of the reservoir, the pressure within the reservoir, and the size of the composition flow path at its narrowest point are arranged so that, when the outlet valve is fully opened, the reservoir will discharge in less than 30 seconds.

9. An inhaler according to claim 1, configured to eject the inhalable composition therefrom in the form of droplets, at least 99% vol of the droplets having a diameter of less than 10 microns.

10. An inhaler according to claim 1, wherein the alcohol is a monohydric alcohol and the inhalable composition further comprises one or more of a glycol and a glycol ether.

11. An inhaler according to claim 10, wherein the ratio of monohydric alcohol to glycol or glycol ether by weight is from 6:1 to 1:1.

12. An inhaler according to claim 1, wherein the inhalable composition comprises one or more cannabinoids or pharmaceutically acceptable derivatives or salts thereof;

a propellant;

a monohydric alcohol; and a glycol and/or glycol ether in a weight ratio of monohydric alcohol to glycol/glycol ether of from 6:1 to 1:1.

13. The inhaler of claim 1 comprising the inhalable composition of claim 12.

* * * * *